(12) United States Patent
Hsu

(10) Patent No.: US 10,272,086 B2
(45) Date of Patent: Apr. 30, 2019

(54) MINOXIDIL FOR SUPPRESSING ANDROGEN RECEPTOR FUNCTION

(71) Applicants: CHANG GUNG MEMORIAL HOSPITAL, LINKOU, Gueishan Township, Taoyuan County (TW); Wilson Hsu, Taoyuan, Taoyuan County (TW)

(72) Inventor: Cheng-Lung Hsu, Gueishan Township, Taoyuan County (TW)

(73) Assignees: Chang Gung Memorial Hospital, Linkou, Linkou (TW); Wilson Hsu, Taoyuan (TW)

( * ) Notice: Subject to any disclaimer, the term of this patent is extended or adjusted under 35 U.S.C. 154(b) by 90 days.

(21) Appl. No.: 14/783,544

(22) PCT Filed: Apr. 30, 2014

(86) PCT No.: PCT/US2014/035983
§ 371 (c)(1),
(2) Date: Oct. 9, 2015

(87) PCT Pub. No.: WO2014/193587
PCT Pub. Date: Dec. 4, 2014

(65) Prior Publication Data
US 2016/0045499 A1 Feb. 18, 2016

Related U.S. Application Data

(60) Provisional application No. 61/817,830, filed on Apr. 30, 2013.

(51) Int. Cl.
| | | |
|---|---|---|
| *A61K 31/506* | (2006.01) |
| *A61K 31/07* | (2006.01) |
| *A61K 31/203* | (2006.01) |
| *A61K 31/65* | (2006.01) |
| *A61K 45/06* | (2006.01) |

(52) U.S. Cl.
CPC .......... *A61K 31/506* (2013.01); *A61K 31/07* (2013.01); *A61K 31/203* (2013.01); *A61K 31/65* (2013.01); *A61K 45/06* (2013.01)

(58) Field of Classification Search
CPC .................................................... A61K 31/506
See application file for complete search history.

(56) References Cited

U.S. PATENT DOCUMENTS

| | | |
|---|---|---|
| 5,183,817 A | 2/1993 | Bazzano |
| 5,780,049 A | 7/1998 | Deckner et al. |
| 6,019,988 A | 2/2000 | Parab et al. |
| 6,419,913 B1 | 7/2002 | Niemiec et al. |
| 7,705,010 B2 | 4/2010 | Black et al. |
| 2010/0174222 A1* | 7/2010 | McDaniel ............ A61B 18/203 604/20 |

FOREIGN PATENT DOCUMENTS

| | | |
|---|---|---|
| WO | 1995011254 A1 | 4/1995 |
| WO | 1998/33472 A1 | 8/1998 |
| WO | WO 2006/091587 A2 * | 8/2006 ............. A61K 39/02 |

OTHER PUBLICATIONS

International Search Report and Written Opinion issued in International Application No. PCT/US2014/035983 dated Aug. 28, 2014.

* cited by examiner

*Primary Examiner* — Wu Cheng W Shen
*Assistant Examiner* — Christopher R Stone
(74) *Attorney, Agent, or Firm* — Osha Liang LLP

(57) ABSTRACT

Methods for treating androgen receptor related diseases and suppressing androgen receptor related function by administering an effective amount of minoxidil are provided. Methods for treating or prophylactically treating acne by administering an effective amount of minoxidil are also provided. An anti-acne medication is optionally administered to treat or prophylactically treat acne.

13 Claims, 11 Drawing Sheets

(A)

(B)

(A) AR-FxxLF peptide interaction (B) AR-ARA54C interaction (E)

(F)

MINOXIDIL FOR SUPPRESSING ANDROGEN RECEPTOR FUNCTION

CROSS-REFERENCE TO RELATED APPLICATIONS

This application is a national stage under 35 U.S.C. 371 based on and claiming the benefit of International Application PCT/US2014/035983, filed on Apr. 30, 2014, which claims the benefit of priority from U.S. Provisional Application No. 61/817,830, filed Apr. 30, 2013, the entire disclosure of each of which is incorporated herein by reference.

TECHNOLOGY FIELD

The present invention relates to the use of minoxidil for suppressing androgen receptor (AR) related function and the treatment of androgen receptor-related diseases.

BACKGROUND OF THE INVENTION

The androgen receptor (AR) is a nuclear receptor that directs gene regulation in response to androgens, including testosterone and its derivative dihydrotestosterone (DHT). The androgen binds to ligand-binding domains (LBD) of the AR. In the absence of androgen, AR resides in the cytosol bound to a complex of heat shock proteins. Circulating androgens diffuse freely into the cytosol and their binding to AR triggers a series of conformational and structural changes of AR that result in nuclear translocation, gene transcription and protein translation. AR signaly plays a central role in growth, differentiation and function of male genitalia, male and female fertility and reproduction. Alterations in the AR gene are associated with other diseases that are not related to fertility and reproduction.

Despite advances made in the diagnosis and treatment of AR-related diseases over the last 50 years, the medical community is still faced with the challenge of treating numerous types of AR-related diseases. Accordingly, there is still a need for a more effective and safe treatment for AR-related diseases. The present invention addresses this need.

BRIEF SUMMARY OF THE INVENTION

The present invention is directed to methods for treating an androgen receptor (AR) related disease in a subject, by administering an effective amount of minoxidil, a pharmaceutically acceptable salt thereof or a prodrug thereof, to the subject to treat AR related disease.

Methods for suppressing AR related function in a cell, a tissue or a subject, by administering an effective amount of minoxidil, a pharmaceutically acceptable salt thereof, a prodrug thereof to the cell, the tissue or the subject to suppress the AR related function are also provided.

Methods for treating or prophylactically treating acne in a subject, the method comprising administering an effective amount of minoxidil, a pharmaceutically acceptable salt thereof, a prodrug thereof or a pharmaceutical composition described herein to the subject to treat or prophylactically treat acne are also provided.

The invention will become more apparent when read with the accompanying figures and detailed description which follow.

BRIEF DESCRIPTION OF THE DRAWINGS

Illustrative embodiments of the present invention are described in detail below with reference to the following Figures.

DETAILED DESCRIPTION

Definitions

Figure 1:
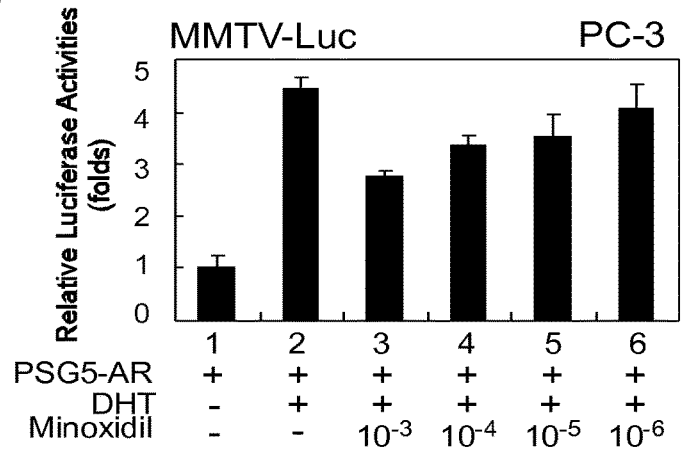
FIG. 1 is an assembly of images illustrating Minoxidil suppresses AR transactivation in MMTV-Luv reporter assay. Panel (a) is a bar graph illustrating the effect of pSG5-AR, dihydrotestosterone (DHT) and various concentrations of Minoxidil in prostate cancer cells (PC-3). Panel (b) is a bar graph illustrating the effect of DHT and Minoxidil in prostate cancer cells (LNCaP).
Figure 1:
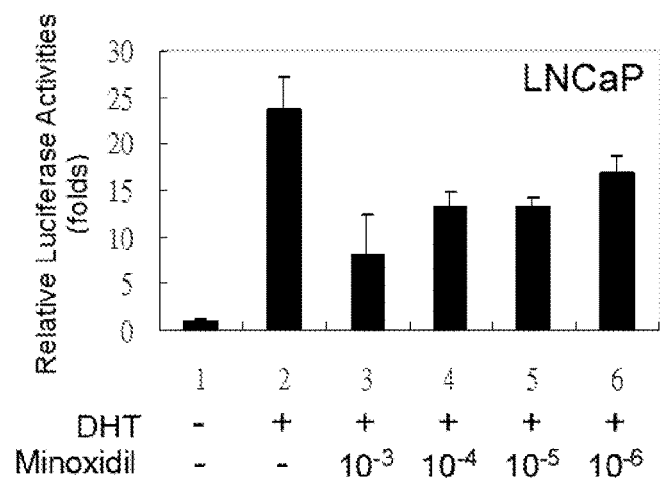

As employed above and throughout the disclosure, the following terms, unless otherwise indicated, shall be understood to have the following meanings.

As used herein, the singular forms "a," "an," and "the" include the plural reference unless the context clearly indicates otherwise.

An "effective amount," as used herein, includes a dose of Minoxidil or a pharmaceutical composition described herein that is sufficient to suppress the function of the androgen receptor or to treat an AR related disease.

The term "treating," "treat," or "treatment" as used herein includes preventative (e.g. prophylactic), palliative, and curative uses or results, wherein the object is to prevent or slow down AR related diseases.

The term "suppressing" or "suppress" includes slowing or reducing the function, activity or response of an androgen receptor, such as intracellular protein expression or interaction.

The term "prodrug" is a pharmacologically inactive compound that is converted into a pharmacologically active agent by a metabolic transformation.

Pharmaceutically acceptable salts of the compound of the invention include salts derived from an appropriate base, such as an alkali metal (for example, sodium, potassium), an alkaline earth metal (for example, calcium, magnesium), ammonium and $NX_4^+$ (wherein X is $C_1$-$C_4$ alkyl). Pharmaceutically acceptable salts of an amino group include salts of organic carboxylic acids, such as tartaric, aliphatic, cycloaliphatic, aromatic, heterocyclic, carboxylic and sulfonic classes of organic acids, such as, for example, formic, glucuronic, malic, maleic, fumaric, pyruvic, aspartic, glutamic, benzoic, anthranilic, mesylic, salicylic, hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, hydroxybutyric, cyclochexylaminosulfonic, galactaric and galacturonic acid and the like, lactobionic, fumaric, and succinic acids; organic sulfonic acids, such as methaniesulfolic, ethanesulfonic, isothionic, benzenylesulfonic and p-toluenesulfonic acids; and inorganic acids such as hydrochloric, hydrobromic, hydroiodic, nitric, carbonic, sulfuric, sulfamic and phosphoric acid and the like. Pharmaceutically acceptable salts of a compound having a hydroxy group consist of the anion of said compound in combination with a suitable cation such as $Na^+$, $NH_4^+$ or $NX_4^+$ (wherein X is, for example, a $C_1$-$C_4$ alkyl group), $Ca^{++}$, $Li^+$, $Mg^{++}$, or, $K^+$ and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound in free form.

The term "androgen receptor related disease" as used herein refers broadly to a condition associated with one or more aspects of androgen receptor structure and/or function. Androgen receptor related disease can be characterized by deviations of the one or more aspects of androgen receptor structure and/or function from normal or baseline levels occurring in a population. These deviations can manifest themselves as abnormalities in structure of androgen receptor, or the activation of the androgen receptor, including altered androgen receptor interaction. The deviations can also manifest themselves as abnormalities in cellular and tissue distribution of androgen receptors, deviations in functioning of androgen receptor, including loss of normal function, gain of toxic function or toxicity, or deviations in regulation of the proteins and cellular pathways related to androgen receptor. Examples of conditions that are currently considered androgen receptor related are AR positive cancer, such as prostate cancer, liver cancer, and breast cancer, acne, benign prostate hyperplasia, polycystic ovarian syndrome, cardiovascular disease, cerebrovascular disease, hypertension, atherosclerosis. It is to be understood that androgen receptor related disease are not limited to the above conditions.

The term "subject" as used herein typically refers to a human or an animal subjected to the methods described herein. It is to be understood that a subject can be a patient with known or suspected androgen receptor related disease, but subjects without known or suspected androgen receptor related disease, such as research subjects, are also included within the scope of the term "subject."

The terms "function" and similar terms, can be used in reference to the activity or the response of an androgen receptor. The function may relate to modification of structure, distribution, responses, processes and cascades in a cell, tissue or organism bearing androgen receptors. The interaction with the androgen receptor may reduce or alter the function of the androgen receptor or result in an increased or decreased response, or both an increased and a decreased response, when assessed through different parameters or processes.

All numbers herein are approximations and may be modified by "about."

Methods of Treating Androgen Receptor Related Disease

Minoxidil (6-piperidin-1-ylpyrimidine-2,4-diamine 3-oxide) was introduced in the 1970s as an anti-hypertension medication and excess hair growth was noted as a side effect. It was subsequently approved by the FDA for topical treatment of androgenic alopecia in men, then in women. The topical formulation is available, for example, under the trade name of Rogain®, commercially available from Pfizer. The mechanism of how Minoxidil cause excess hair growth was not clear, but the following mechanisms have been postulated: vasodilatation, angiogenesis, enhanced cell proliferation, and opening of potassium channel. Previous studies have consistently concluded that minoxidil does not act directly through an androgen effect (Nuck A G et al., Topical Minoxidil does not act as an antiandrogen in the flank organ of the gold Syrian hamster. Archives of dermatology. 1987; 123 (1):59-61. Messenger A G et al., Minoxidil: Mechanisms of action on hair growth. The British Journal of Dermatology. 2004; 150 (2): 186-194.)

It was discovered by the inventor that Minoxidil binds to AR and leads to suppression of AR related function, such as transcription and protein expression.

Methods of treating an AR related disease are provided herein by administering an effective amount of Minoxidil, a pharmaceutically acceptable salt thereof or a prodrug thereof to treat the AR related disease. Not being bound by any particular theory, it is believed that the therapeutic effect of Minoxidil is by inhibiting AR modulated transcription and translation in the cell.

Non limiting examples of AR related disease are: androgen receptor (AR) positive cancer, dermatological disorder or benign prostate hyperplasia (BPH), cardiovascular disease, cerebrovascular disease, hypertension, atherosclerosis.

In one embodiment, the AR positive cancer is selected from breast cancer, prostate cancer and liver cancer. In another embodiment, the subject is substantially free of central nervous system cancer, such as brain tumor. In another embodiment, the dermatological disorder is acne.

For administration according to the methods provided herein, Minoxidil is administered either alone or in combination with one or more anti-cancer agents. The anti-cancer agent includes conventional chemotherapeutic agent, target cancer therapy or radiation therapy.

The conventional chemotherapeutic agent comprises anthracycline antibiotic, DNA synthesis inhibitor, alkylating agent, antifolate agent, metabolic inhibitor or combination thereof.

The target cancer therapy are medications which inhibit the growth of cancer cells by interfering with specific targeted molecules needed for carcinogenesis and cancer growth, rather than by simply interfering with rapidly dividing cells (e.g. with conventional chemotherapeutic agent).

The target cancer therapy comprises kinase inhibitor, angiogenesis inhibitor, epidermal growth factor receptor (EGFR) inhibitor, HER2/neu receptor or the combination thereof.

The dosage of Minoxidil and anti-cancer agent varies in accordance with the age, weight, comorbidity and condition of the subject to be treated. In one embodiment, the effective amount of Minoxidil is about 5 mg to about 100 mg per day.

Methods of Suppressing Androgen Receptor Related Function

Methods of suppressing AR related function in a cell, a tissue or a subject are provided herein by administering an effective amount of Minoxidil, a pharmaceutically acceptable salt thereof or a prodrug thereof to suppress androgen receptor related function in the cell, the tissue or the subject.

Without being bound by any theory, Minoxidil suppresses AR related function by one or more of the following mechanisms: inhibit AR transactivation, suppress AR gene transcription, suppress AR coactivator (e.g. ARA54C) or FxxLF peptide interaction with AR, reduce AR NH2- and COOH-terminal (N—C) interaction and reduce AR stability.

In various embodiments of the methods provided herein, Minoxidil is administered to suppress AR modulated transcription or translation function, in a cell, a tissue or a subject, which can have a beneficial effect in a subject, such as, but not limited to, inhibiting cancer cell growth or suppressing human hair dermal papilla cell. The use of Minoxidil to suppress AR related function may lead to the reduction of symptoms and signs of AR related disease, slowing down the progression of AR related disease, and increasing the lifespan of the subject having AR related disease.

The methods provided herein encompass therapeutic methods and uses, including methods of treating or attenuating AR related disease, and prophylactic methods, including methods of preventing or reducing the probability of AR related disease in a subject. The methods provided herein also encompass research methods and uses, including in vitro, ex vivo or in vivo methods of suppressing AR related function in the cell, the tissue or the subject.

Pathological cells bearing AR, such as hyperproliferative cells or tissue may be treated by contacting the cells or tissue with an effective amount of Minoxidil or the pharmaceutical composition of this invention. The cells with AR, such as prostate cancer cells, can be primary cancer cells or can be cultured cells available from tissue banks such as the American Type Culture Collection (ATCC). The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

In vitro efficacy of Minoxidil or the pharmaceutical composition described herein can be determined using methods well known in the art. For example, the cytoxicity of Minoxidil may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65: 55 63, 1983. The cytoxicity of Minoxidil may be studied by colony formation assay. Functional assays for binding Minoxidil may be performed via ELISA. Cell cycle block by Minoxidil may be studied by standard propidium iodide (PI) staining and flow cytometry. Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays. Assays can also be done in vivo using a murine model. See, e.g., Teicher, B., Tumor Models for Efficacy Determination. Mol Cancer Ther 2006; 5:2435-2443."

Methods for Treating or Prophylactically Treating Acne

Methods for treating or prophylactically treating acne are provided herein by administering an effective amount of Minoxidil, a pharmaceutically acceptable salt thereof, a prodrug thereof, or a pharmaceutical composition as described herein to treat acne.

In one embodiment, Minoxidil, a pharmaceutically acceptable salt thereof, a prodrug thereof, or the pharmaceutical composition described herein is administered topically to the affected area about once a day to about three times a day.

Pharmaceutical Composition

Pharmaceutical compositions for treating or prophylactically treating acne are provided herein. The pharmaceutical compositions provided herein are useful for treating or prophylactically treating acne, preferably by advantageous synergistic effects of the combinations.

In one embodiment, the pharmaceutical composition includes Minoxidil, a pharmaceutically acceptable salt thereof or a prodrug thereof, and an anti-acne medication. Non limiting examples of anti-acne medication include vitamin A, one or more antibiotics, oral contraceptives and retinoids.

In one embodiment, the retinoid is isotretinoin. In another embodiment, the antibiotic is tetracycline or a derivative thereof. In another embodiment, the antibiotic is minocycline or a derivative thereof. In yet another embodiment, the antibiotic is doxycycline or a derivative thereof.

The pharmaceutical compositions to be administered according to the methods of some embodiments provided herein can be formulated with, prepared with, or administered with, a pharmaceutically acceptable carrier. Such preparations may be prepared by various techniques. Such techniques include bringing into association active components (such as Minoxidil and antibiotic) of the pharmaceutical compositions and an appropriate carrier. In one embodiment, pharmaceutical compositions are prepared by uniformly and intimately bringing into association active components of the pharmaceutical compositions with liquid carriers, with solid carriers, or with both. Liquid carriers include, but are not limited to, aqueous formulations, non-aqueous formulations, or both. Solid carriers include, but are not limited to, biological carriers, chemical carriers, or both.

The pharmaceutical compositions are administered in an aqueous suspension, an oil emulsion, water in oil emulsion and water-in-oil-in-water emulsion, and in carriers including, but not limited to, creams, gels, foams, liposomes (neutral, anionic or cationic), lipid nanospheres or microspheres, neutral, anionic or cationic polymeric nanoparticles or microparticles, site-specific emulsions, long-residence emulsions, sticky-emulsions, micro-emulsions, nano-emulsions, microspheres, nanospheres, nanoparticles and minipumps, and with various natural or synthetic polymers that allow for sustained release of the pharmaceutical composition including anionic, neutral or cationic polysaccharides and anionic, neutral cationic polymers or copolymers, the minipumps or polymers being implanted in the vicinity of where composition delivery is required. Furthermore, the active components of the pharmaceutical compositions provided herein are useful with any one, or any combination of, carriers. These include, but are not limited to, anti-oxidants, buffers, and bacteriostatic agents, and optionally include suspending agents and thickening agents.

For administration in a non-aqueous carrier, active components of the pharmaceutical compositions provided herein are emulsified with a mineral oil or with a neutral oil such as, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the number of fatty acid carbons is between 12 and 22 and wherein the fatty acids can be saturated or unsaturated. Optionally, charged lipid or phospholipid are suspended in the neutral oil. A suitable phospholipid is, but is not limited to, phosphatidylserine, which targets receptors on macrophages. The pharmaceutical compositions provided herein are optionally formulated in aqueous media or as emulsions using known techniques.

The pharmaceutical compositions provided herein may include Minoxidil described herein and optionally, other therapeutic and/or prophylactic ingredients. The carrier and other therapeutic ingredients must be acceptable in the sense of being compatible with the other ingredients of the composition and not deleterious to the recipient thereof.

The pharmaceutical compositions are administered in an amount effective to treat or prophylactically treat acne. The dosage of the pharmaceutical composition administered will depend on the severity and the location of acne being treated, the particular formulation, and other clinical factors such as weight and condition of the recipient and route of administration. In one embodiment, the amount of the pharmaceutical composition administered corresponds from about 1% to 10% of Minoxidil. In another embodiment, the amount of the pharmaceutical composition administered corresponds to about 2%, 3%, 4%, 5%, 6%, 7%, 8%, 9% of Minoxidil or any % therebetween in 0.1% increments. In a further embodiment, the amount of the pharmaceutical composition administered corresponds to about 5% of Minoxidil.

In accordance with the methods provided herein, the pharmaceutical compositions is delivered by a variety of routes including, but not limited to, injection (e.g., subcutaneous, intramuscular, intravenous, intra-arterial, intraperitoneal); continuous intravenous infusion; topical (cutaneously, dermally, transdermally); orally (e.g., tablet, pill, liquid medicine, edible film strip); implanted osmotic pumps; suppository; aerosol spray, impression into skin and electroporation. In one embodiment, the pharmaceutical composition is applied topically to treat or prophylactically treat acne.

A pharmaceutical composition may be administered in a single dose treatment or in multiple dose treatments, on a schedule, or over a period of time appropriate to the disease being treated, the condition of the recipient and the route of administration. The desired dose may conveniently be presented in a single dose or as divided doses administered at appropriate intervals, for example, as two, three, four or more sub-doses per day. The sub-dose itself may be further divided, e.g., into a number of discrete loosely spaced administrations Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated. Some of the procedures are described below for illustrative purpose.

Description of Materials and Methods Used in the Examples

The following materials and methods were used in the Examples described below.

Cell Culture: Prostate cancer cell lines (PC-3 and LNCaP) and human hair dermal papilla cells were used throughout the experimental studies. Human prostate cancer cell lines (PC-3 and LNCaP) were grown in Dulbecco's minimal essential medium, which was supplemented with 10% fetal bovine serum. Human hair dermal papillae cells (HHDPC) were maintained in RPMI medium with 10% fetal calf serum. Prostate cancer cells ($1 \times 10^5$) were seeded in each well of a 24-well plate and incubated overnight in a 37° C. incubator with 5% $CO_2$.

Cell Transcription Assay: In Examples 1, 3, 4 and 6, the mouse mammary tumor virus-luciferase (MMTV-Luc) Reporter Assay (Promega, Madison, Wis.) was used to measure luciferase activity. Luciferase is commonly used as a reporter to assess the AR regulated transcriptional activity in cells.

In Example 2, the prostate specific antigen-luciferase (PSA-Luc) Reporter Assay (Promega, Madison, Wis.) was used to measure luciferase activity.

Statistical Analysis: The statistical significance was calculated by analysis of variance (t-test). The difference between groups was considered to be significant if the P value was <0.05.

EXAMPLES

Example 1: Minoxidil Suppresses AR Transactivation in Prostate Cancer Cells

An in vitro evaluation of the effect of Minoxidil on prostate cancer cell AR transactivation was performed. Prostate cancer cells were cultured as previously described. PC-3 cells were transfected with 300 ng of pSG5-AR and 700 ng of MMTV-LUC reporter plasmid (described in K. Nishimura et al., (2003) "Modulation of androgen receptor transactivation by gelsolin: a newly identified androgen receptor coregulator." *Cancer Res* 63 (16): 4888-4894 and S. Yeh et al., (1996) "Cloning and characterization of a specific coactivator, ARA70, for the androgen receptor in human prostate cells." *Proc Natl Acad Sci USA* 93 (11): 5517-5521) using Superfect kit (purchased from Qiagen Science, Md., USA) according to the manufacturer's instructions, whereas LNCaP cells were transfected with 1000 ng of MMTV-LUC reporter plasmid (described in K. Nishimura et al. 2003 and S. Yeh et al. 1996) using Superfect kit.

The transfected prostate cancer cells were incubated for 16 h, then treated with ethanol and/or 1 nM DHT, with or without $10^{-3}$ to $10^{-6}$ M of Minoxidil for another 16 h.

The prostate cancer cells were harvested and luciferase activity was measured using MMTV-Luc Reporter Assay. FIGS. 1(a) and 1(b) show that DHT enhances Luciferase activity and AR regulated transcription in prostate cancer cells, whereas Minoxidil reduces AR regulated Luciferase activity in the presence of DHT, in a dose dependent manner.

Example 2: Minoxidil Suppresses AR Regulated Transcription and Translation in Prostate Cancer Cells An in vitro evaluation of the effect of Minoxidil on AR transcription was performed. Prostate cancer cells were cultured as previously described.

Figure 2A:
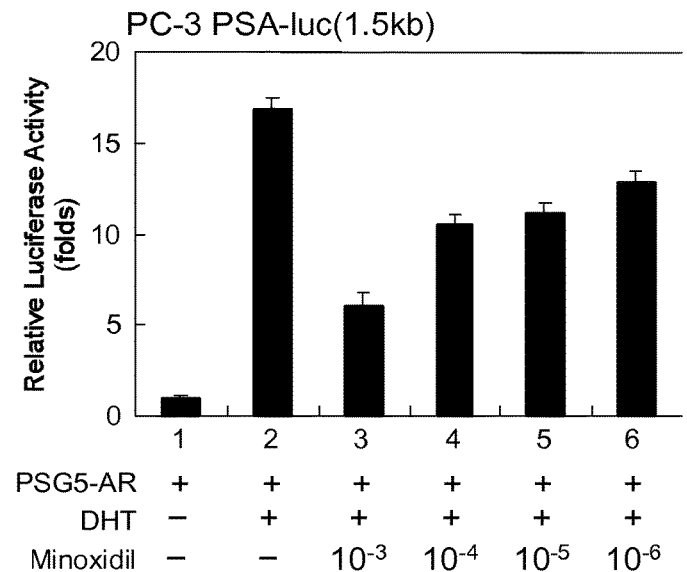
FIG. 2 is an assembly of images illustrating the suppressive effect of Minoxidil on AR gene transcription and protein expression. Panel (a) is a bar graph illustrating the effect of pSG5-AR, dihydrotestosterone (DHT) and various concentrations of Minoxidil on AR transcription in prostate cancer cells (PC-3). Panel (b) is a photograph of Western blot analysis showing the effect of various concentrations of Minoxidil on AR protein and PSA (prostate specific antigen) expression in prostate cancer cells (LNCaP). Pane (C) is a bar graph illustrating the effect of 500 ng of pSG5-AR, various concentrations of Minoxidil and the hormone dexamethasone (Dexan, 1 uM) on PC-3 cells.

PC-3 cells were transfected with 300 ng pSG5-AR and 700 ng PSA-Luc (1.5 kb) plasmids (described in K. Nishimura et al. 2003 and S. Yeh et al. 1996) using Superfect kit and incubated for 16 h. The transfected prostate cancer cells were treated with ethanol, pSG5-AR and/or 1 nM DHT, with or without $10^{-3}$ to $10^{-6}$ M of Minoxidil for another 16 h and harvested for luciferase activity. FIG. 2(A) shows that DHT enhances Luciferase activity and AR regulated transcription in prostate cancer cells, whereas Minoxidil is effective in reducing Luciferase activity and AR regulated transcription in the presence of DHT, in a dose dependent manner.

Prostate cancer cells (LNCaP) were treated with DMSO or $10^{-3}$~$10^{-5}$ M of Minoxidil for 24 h. The cells were prepared for electrophoresis on SDS/PAGE gel and then transferred onto nitrocellulose (Minipore, Billerica, USA).

AR, PSA and beta-actin proteins were identified using anti-AR (N-20 from Santa Cruz Biotechnology, Santa Cruz, USA), anti-PSA (C-19 from Santa Cruz Biotechnology, Santa Cruz, USA), or anti-tubulin (MAB1501 from Millipore, Billerica, USA) respectively. Images were shown using alkaline phosphatase substrate color kit (Bio-Rad, Hercules, USA).

Figure 2B:
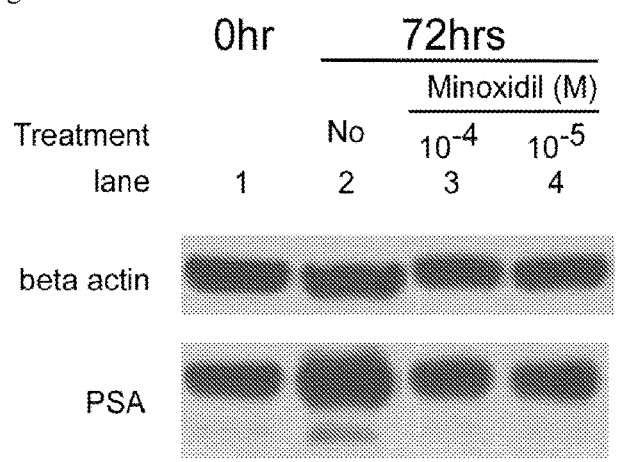

FIG. 2(B) shows Minoxidil is effective in inhibiting AR regulated PSA protein expression in the presence of DHT, in a dose dependent manner.

Figure 2C:
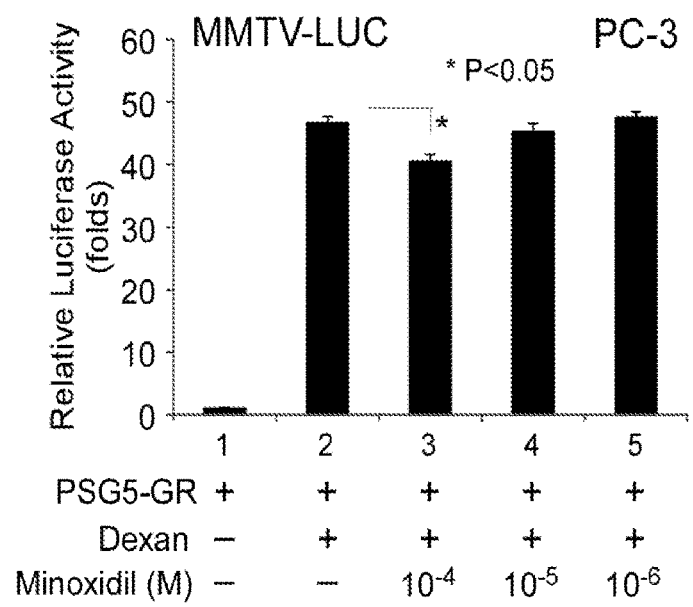

To assess possible nonspecific effects of minoxidil at high concentrations, a control study was performed testing different concentrations of minoxidil (1-100 µM) on glucocorticoid receptor (GR) transcriptional activity. As shown in FIG. 2C, the highest concentration minoxidil (100 µM) did affect GR transcriptional activity in reporter assays in PC-3 cells, whereas lower concentrations (1-10 µM) did not. These data suggest that minoxidil, a small hydrophobic molecule, may have multiple targets in the cell when used at high concentrations.

Example 3: Minoxidil Suppresses AR Cofactor Interaction in Prostate Cancer Cells Many AR coactivators bind to ligand binding domain of AR via FxxLF-like motif to enhance AR transactivation. ARA54C is an AR coactivator that has been shown with high ligand induced affinity for AR. The interaction between ARA54C and AR is mediated by the FxxLF motif in the AR ligand binding domain.

An in vitro evaluation of Minoxidil on AR cofactor interaction was performed in prostate cancer cells. Prostate cancer cells (PC-3) were cultured as previously described. PC-3 cells were transfected with 300 ng of pG5-LUC reporter gene plasmid (described in K. Nishimura et al. 2003 and S. Yeh et al. 1996), 350 ng of AR coactivator (ARA54C) or peptide (FxxLF) in pCMX-GAL4 vector and 350 ng of VP16-AR using Superfect kit and incubated for 16 h.

The transfected prostate cancer cells were treated with ethanol and 1 nM DHT, with or without $10^{-3}$~$10^{-5}$ M of Minoxidil for another 16 h. The interactions of AR-FxxLF peptide and AR-ARA54C were detected using Mammalian two-hybrid assay and luciferase activity was measured using MMTV-Luc Reporter Assay.

Figure 3:
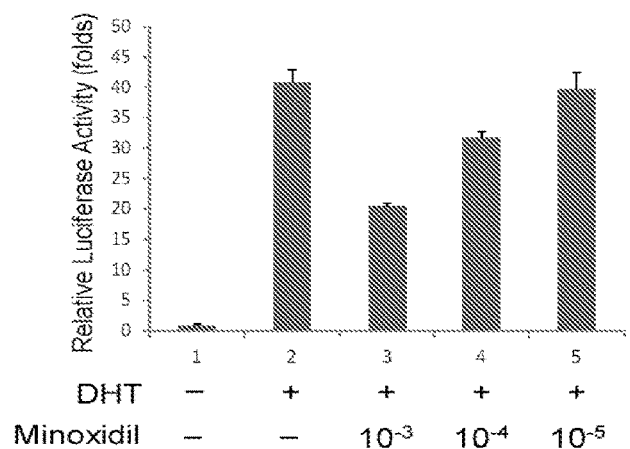
FIG. 3 is an assembly of images illustrating the suppressive effect of Minoxidil on peptide-AR and cofactor-AR interaction in prostate cancer cells (PC-3). Panel (a) is a bar graph illustrating the effect of DHT and various concentrations of Minoxidil on AR-FxxLF peptide interaction. Panel (b) is a bar graph showing the effect of DHT and various concentrations of Minoxidil on AR-cofactor-AR (ARA54C) interaction.
Figure 3:
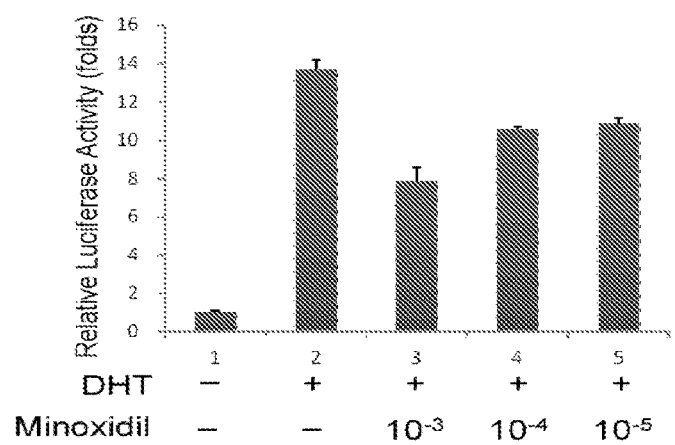

FIG. 3(A) shows Minoxidil suppresses the FxxLF-containing peptide interaction with AR in the presence of DHT and hence, a reduction in Luciferase activity in a dose dependent manner. FIG. 3(B) shows Minoxidil suppresses the interaction of ARA54C coactivator with AR in the presence of DHT and hence, a reduction in Luciferase activity in a dose dependent manner.

Example 4: Minoxidil Suppresses AR NH-2 and COOH-terminal (N—C) Interaction

AR NH2- and COOH-terminal (N—C) interaction was important for full AR related function, which is mediated by the AR N-terminal FxxLF motif. An in vitro assessment of Minoxidil on AR N—C interaction was performed in prostate cancer (PC-3) cells.

PC-3 cells were cultured as previously described and transfected with 300 ng of pG5-LUC reporter gene plasmid, 350 ng of plasmid pCMX-GAL4-AR-C (a.a. 663~919) (described in K. Nishimura et al. 2003 and S. Yeh et al. 1996) and 350 ng of VP16-AR-N (a.a 1~506)) using Superfect kit and incubated for 16 h.

The transfected prostate cancer cells were treated with ethanol and 1 nM DHT, with or without $10^{-3}$~$10^{-6}$ M of Minoxidil for another 16 h. The N—C interactions were detected using Mammalian two-hybrid assay and luciferase activity was measured using MMTV-Luc Reporter Assay.

Figure 4:
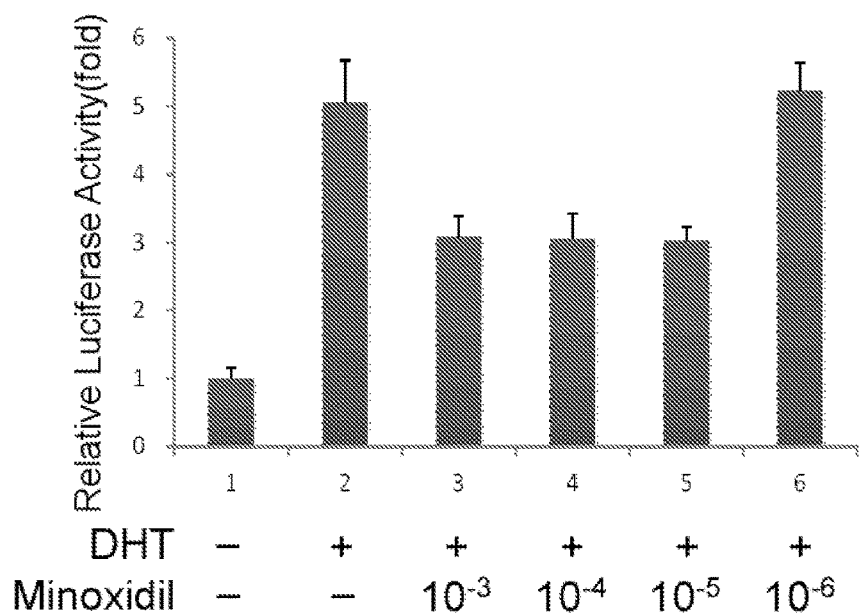
FIG. 4 contains a bar graph illustrating various concentrations of Minoxidil suppress AR NH-2 and COOH-terminal (N—C) interaction in prostate cancer cells (PC-3).

FIG. 4 shows Minoxidil at concentration ranging from 10 to 100 uM suppresses the N—C interaction in the presence of DHT and hence, a reduction in Luciferase activity in prostate cancer cells. This suggests that Minoxidil also disrupts AR N- and C-terminal interactions, providing an additional mechanism for Minoxidil suppression of AR-related function.

Example 5: Minoxidil Reduces AR Stability in Prostate Cancer Cells

An in vitro assessment of Minoxidil on AR stability was performed in prostate cancer cells (LNCaP).

LNCaP cells were cultured as previously described and treated with DMSO or $10^{-3}$~$10^{-5}$ M of Minoxidil for 24 h. The cells were prepared for electrophoresis on SDS/PAGE gel and then transferred onto nitrocellulose.

AR and beta-actin proteins were identified using anti-AR or anti-tubulin respectively. Images were illustrated using alkaline phosphatase substrate color kit.

Figure 5A:
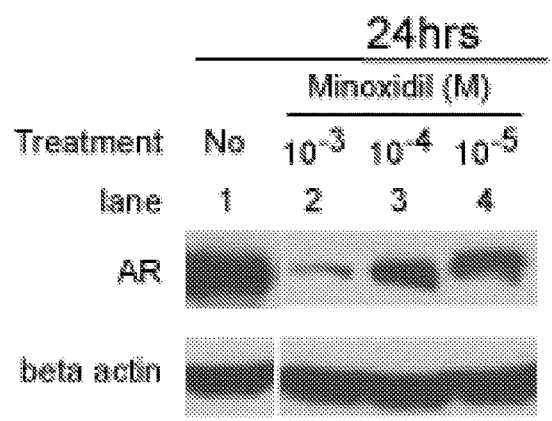
FIG. 5A contains an assembly of Western blot photographs illustrating Minoxidil reduces AR stability in prostate cancer cells (LNCaP) in a dose dependent manner.

FIG. 5A illustrates Minoxidil reduces AR stability in the presence of DHT, in a dose dependent manner.

Figure 5B:
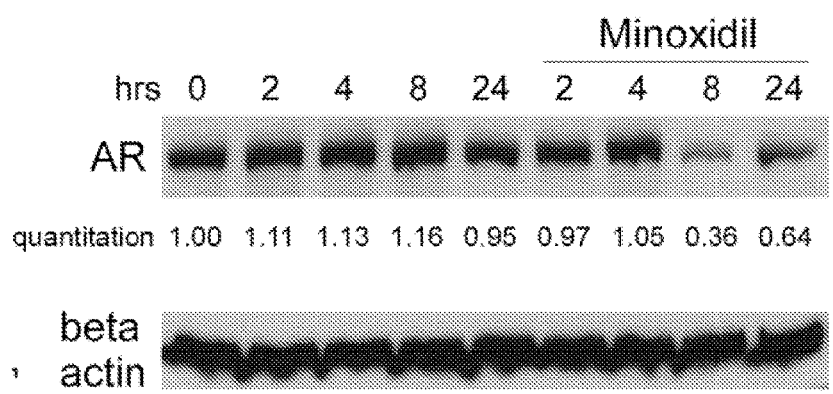
FIG. 5B is an assembly of Western blot photographs for Minoxidil pulse-chase time-course studies.

As shown in FIG. 5B, minoxidil induced a decrease in AR protein that was most evident 8 h after treatment, at which point AR protein levels were 36% of pretreatment values. These observations suggest that the mechanism of action of minoxidil may include a decreased in AR stability.

Example 6: Minoxidil Suppresses AR Transactivation in Human Hair Dermal Papilla Cells An in vitro assessment of the effect of Minoxidil on dermal papilla cell AR transcription was performed. Human hair dermal papilla cells were cultured as previously described and transfected with 300 ng of pSG5-AR and 700 ng of MMTV-LUC reporter plasmid (described in K. Nishimura et al. 2003 and S. Yeh et al. 1996) using Superfect kit.

The transfected human hair dermal papilla cells (HH-DPCs) were incubated for 16 h, then treated with 1 nM DHT and one of the following: bicalultamide (an non-steroidal anti-androgen medication) or $10^{-3}$ to $10^{-5}$ M of Minoxidil for another 16 h.

Figure 6:
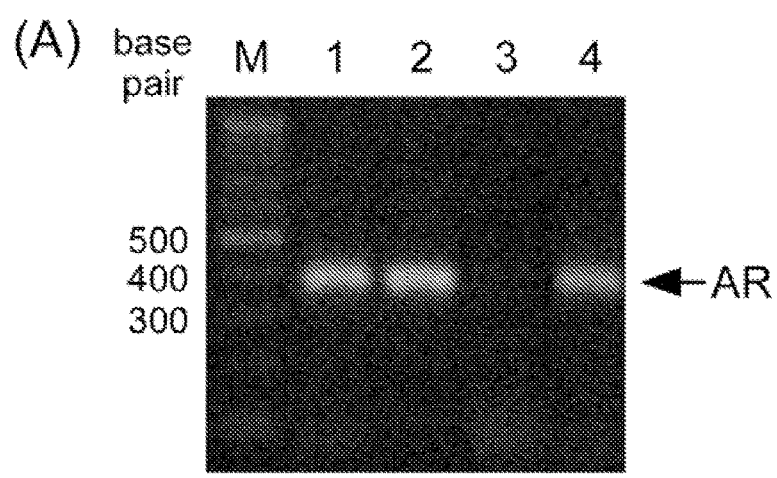
FIG. 6A-6F is an assembly of images illustrating Minoxidil suppresses AR transactivation in skin cells.
Figure 6:
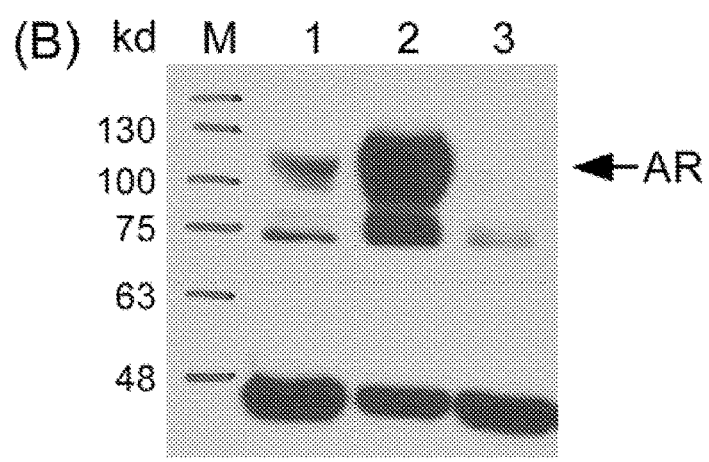
Figure 6:
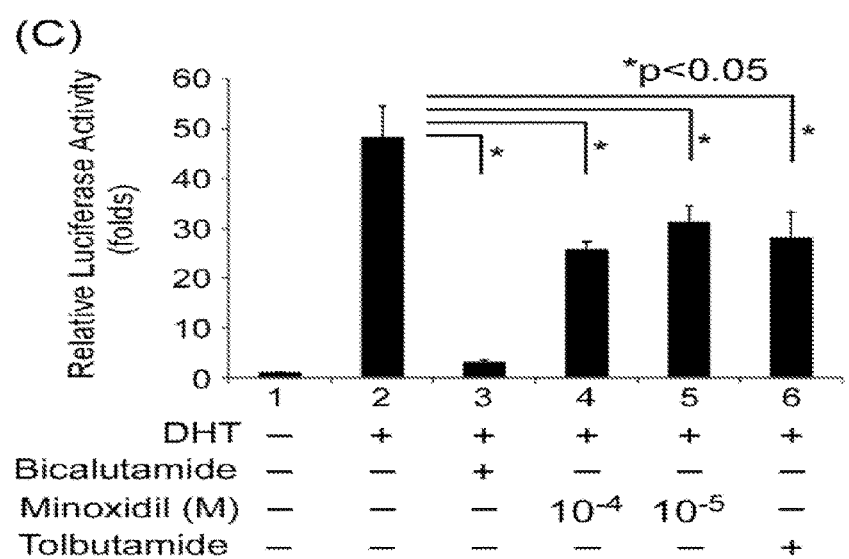
Figure 6:
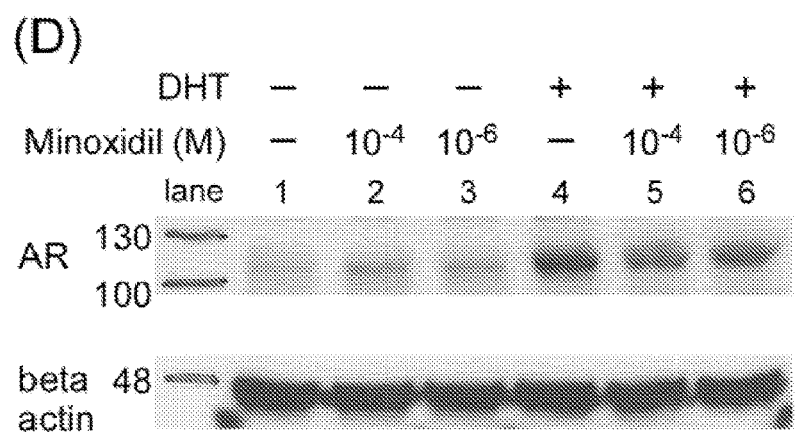
Figure 6:
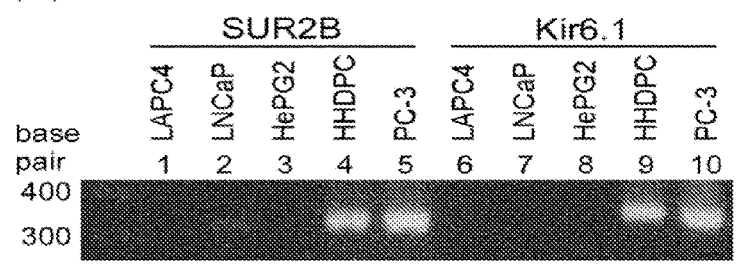
Figure 6:
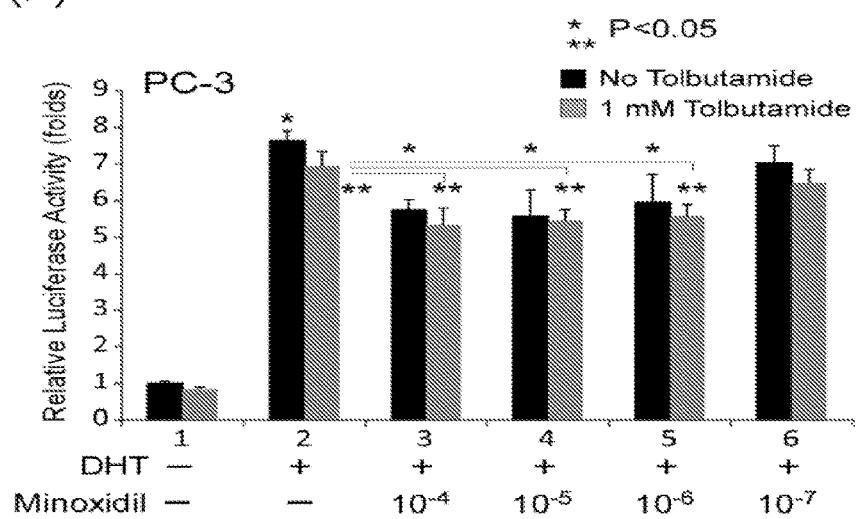

HHDPCs cells were harvested and luciferase activity was measured using MMTV-Luc Reporter Assay. FIGS. 6A and 6B show AR expression in HHDPCs at mRNA and protein levels respectively. As shown in FIG. 6C, Minoxidil suppressed AR transcriptional activity in a concentration-dependent manner (compare lanes 4 and 5 to lane 2). The suppression of AR transactivation in dermal papilla cells was statistically significant using $10^{-3}$ and $10^{-4}$ M of Minoxidil. The effect of minoxidil on AR protein stability in HHDPCs is illustrated in FIG. 6D, which shows Minoxidil induced a concentration-dependent reduction in AR protein stability. These data provide further evidence that the efficacy of minoxidil in treating AGA may involve suppression of AR-related functions.

Minoxidil has been proposed to act as a potassium channel opener in the context of AGA treatment, an action that is primarily associated with the SUR2B/Kir6.1 potassium channel subtype in hair follicles (Shorter K, et al., Human hair follicles contain two forms of ATP-sensitive potassium channels, only one of which is sensitive to minoxidil. FASEB journal: official publication of the Federation of American Societies for Experimental Biology. 2008; 22 (6):1725-1736). Tolbutamide, a potassium channel blocker that has been reported to antagonize minoxidil effects on hair growth. suppressed AR transcriptional activity in a reporter assay in HHDPCs, as shown in FIG. 6C (compare lane 3 to lane 2). Tests of HHDPCs and various cancer cell lines further showed that HHDPCs expressed the same subtype of potassium channel as that found in the prostate cancer cell line PC-3, which lacks an endogenous AR (FIG. 6E). Notably, minoxidil suppressed AR transcriptional activity in PC-3 cells, but this effect was not blocked by tolbutamide (FIG. 6F), suggesting that the suppressive effect of minoxidil on AR transcriptional activity is not a potassium channel-related action.

Figure 7A:
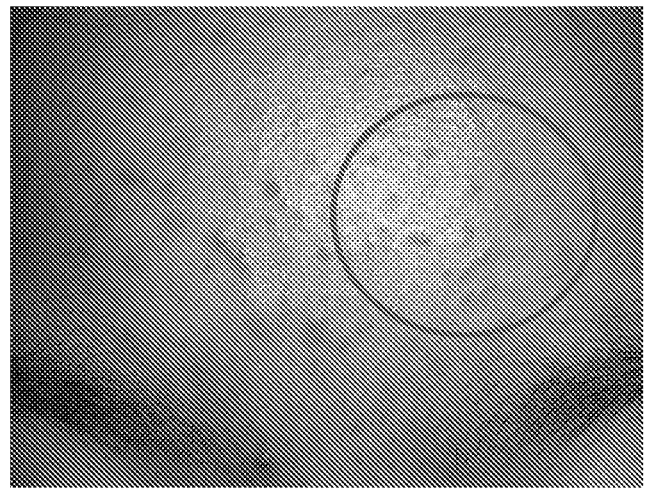
FIG. 7(A) was taken before the commencement of 5% topical Minoxidil treatment and FIG. 7B was taken after a 7-day course of 5% topical Minoxidil treatment. The photographs show a faster healing time and less acne break out after Minoxidil treatment.
Figure 7B:
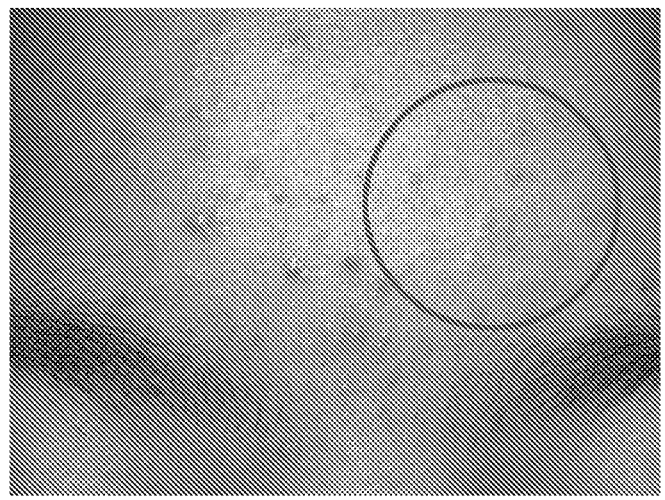
FIG. 7 is an assembly of photographs illustrating the effect of 5% topical Minoxidil on acne.
Figure 8A:
FIG. 8 is an assembly of photographs showing 5% topical Minoxidol is effective in treating acne over a 48-hour period.
Figure 8B:
Figure 8C:

Example 7: The Use of Topical Minoxidil to Treat and Prophylactically Treat Acne An in vivo evaluation of topical Minoxidil on acne was carried out in a female patient. FIG. 7(A) was taken before the commencement of topical Minoxidil treatment, which shows a patient with multiple pimples on her forehead. 5% Minoxidil solution was applied topically to the left forehead (red circle) once a day for 7 days, and the right forehead was the control side. FIG. 7B was taken after the 7-day course Minoxidil treatment, which shows the disappearance of pimples on the left (treated) forehead. In addition, there was less new pimple formation on the left (treated) forehead compared to the right (untreated) forehead.

This result suggests that topical Minoxidil treatment is effective in treating and prophylactically treating acne.

Example 8: The Use of Minoxidil to Treat Acne

5% Minoxidil was applied topically to an acne on a patient's face. The left panel shows a photograph taken before the commencement of the treatment, the middle panel shows a photograph taken after one application of 5% Minoxidil and the right panel shows a photograph taken after two applications of 5% Minoxidil, which shows significant reduction in erythema and swelling around the acne. These photographs show that 5% Minoxidil is effective in treating acne.

Example 9: Topical Minoxidil Administration Reduces the Symptoms and Signs of Acne in a Clinical Trial A double-blind clinical trial is conducted, in which topical Minoxidil and placebo are administered to patients with acne. Patients receiving topical Minoxidil show a statistically significant reduction in the symptoms and signs of acne, in comparison with the placebo group.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. The subject matter should be understood by reference to appropriate portions of the entire specification, any or all drawings and each claim.

What is claimed is:

1. A method for treating acne, consisting of administering an effective amount of minoxidil or a pharmaceutically acceptable salt thereof to a subject in need thereof.

2. The method of claim 1, wherein the effective amount of minoxidil is about 5 mg to about 100 mg per day.

3. A method for treating acne, consisting of administering an effective amount of minoxidil or a pharmaceutically acceptable salt thereof and an anti-acne medication selected from the group consisting of vitamin A, antibiotic, oral contraceptive, and retinoid to a subject in need thereof, wherein the erythema or swelling of acne is reduced.

4. The method of claim 3, wherein said administering is topical administration.

5. The method of claim 4, wherein the topical administration is once a day to three times a day.

6. The method of claim 3, wherein the anti-acne medication is vitamin A.

7. The method of claim 3, wherein the anti-acne medication is one or more antibiotics.

8. The method of claim 7, wherein the antibiotic is tetracycline or a derivative thereof.

9. The method of claim 7, wherein the antibiotic is minocycline or a derivative thereof.

10. The method of claim 7, wherein the antibiotic is doxycycline or a derivative thereof.

11. The method of claim 3, wherein the anti-acne medication is an oral contraceptive.

12. The method of claim 3, wherein the anti-acne medication is a retinoid.

13. The method of claim 12, wherein the retinoid is isoretinoin.

* * * * *